United States Patent [19]

Masuda et al.

[11] Patent Number: 5,128,354
[45] Date of Patent: Jul. 7, 1992

[54] AGENT FOR TREATING ISCHEMIC BRAIN DAMAGE

[75] Inventors: Yoshinobu Masuda, Katano; Toshiaki Kadokawa, Hirakata; Mikio Kurokawa, Kobe; Kayoko Zushi, Hirakata; Yoshiaki Ochi, Sanda, all of Japan

[73] Assignee: Dainippon Pharmaceutical Co., Ltd., Osaka, Japan

[21] Appl. No.: 499,444

[22] PCT Filed: Dec. 27, 1988

[86] PCT No.: PCT/JP88/01335
§ 371 Date: Jun. 25, 1990
§ 102(e) Date: Jun. 25, 1990

[87] PCT Pub. No.: WO89/06129
PCT Pub. Date: Jul. 13, 1989

[30] Foreign Application Priority Data
Dec. 29, 1987 [JP] Japan ............................ 62-335149

[51] Int. Cl.$^5$ ............................................. A61K 31/42
[52] U.S. Cl. .................................................. 514/379
[58] Field of Search .............................. 514/380, 379

[56] References Cited
U.S. PATENT DOCUMENTS
4,172,896 10/1979 Uno et al. ...................... 424/272

OTHER PUBLICATIONS

Y. Masuda et al., "3-Sulfamoylmethyl-1,2-benzisoxazole, . . . ," Arzneim, Forsch./Drug. Res., 30(I), pp. 477-483, 1980.
G. A. King et al., "Protection against Hypoxia-Induced . . . ," J. Clin. Exp. Med., 144, pp. 917-918, Mar. 19, 1988.
A. Fukuda et al., "Protective Effect of Anti-convulsant . . . ," J. Clin. Exp. Med., 144, pp. 917-918, Mar., 1988.

*Primary Examiner*—Fredrick E. Waddell
*Assistant Examiner*—Diane Gardner
*Attorney, Agent, or Firm*—Birch, Stewart, Kolasch & Birch

[57] ABSTRACT

The present invention provides an agent for treating ischemic brain damage comprising 3-sulfamoylmethyl-1,2-benzisoxazole or its alkali metal salt as an active ingredient. This agent can be used for the prevention and/or treatment of cerebral ischemia-induced intracranial diseases or various symptoms associated therewith in mammals including human beings.

4 Claims, No Drawings

AGENT FOR TREATING ISCHEMIC BRAIN DAMAGE

TECHNICAL FIELD

The present invention relates to an agent for treating ischemic brain damage containing a 1,2-benzisoxazole derivative as an active ingredient.

BACKGROUND ART

Unlike other organs, the brain exists under a particular environment: it is immersed in the cerebrospinal fluid within rigid bodies such as the skull and cerebral pachymeninx. It is one of the most active organs in energy metabolism and shows the highest rate of oxygen consumption out of all organs. Most of energy required for the brain neurons are derived from oxygen and glucose. These energy sources are scarcely stored in the brain and continuously supplied by the blood. Therefore, in the cerebral blood vessel itself, the mechanism for controlling cerebral blood flow develops well to stably supply energy sources for brain tissues and to maintain an external environment of the brain neurons constant. When the homeostatic mechanism in the brain is damaged by physical pressure such as hematoma, cerebral tumor or cerebral injury, the brain is placed in the situation of ischemia, and their neurons are exposed to hypoxic situation and cannot function properly. When the brain neurons fall into oxygen-deficiency state (hereinafter referred to as "cerebral hypoxia"), the permeability of membranes of the brain neurons changes; so the invasion of the extracellular fluid causes edema. When cerebral edema grows to a certain extent, the intracranial pressure rises to cause cerebral circulatory disturbance. The augmentation of cerebral hypoxia and the deficiency of glucose and accumulation of its metabolites, which are due to the cerebral circulatory disturbance, enlarge cerebral edema. As a result, the growth of cerebral edema and the rise of intracranial pressure are further accelerated; the compression of brain stem and the disturbance in pass of the cerebrospinal fluid occur and lead to the formation of a vicious circle of the augmentation of cerebral hypoxia, the growth of cerebral edema and the rise of intracranial pressure. Consequently, the lesion is enlarged so that even healthy brain tissues become hypoxic. In the end, the brain falls into the situation of circulatory insufficiency; so the damage is severe. This is the reason why cerebral hypoxia is called the common denominator of most diseases due to cerebral circulatory disturbances [Eur. Neurol.,17 (Supple.1), 113-120 (1978)].

With an increase of the proportion of the elderly in population, senile dementia is becoming a major problem of society. The great majority of senile dementia are composed of cerebrovascular dementia, Alzheimer-type dementia and the mixture thereof. Cerebrovascular dementia appears as secondary disease after cerebrovascular disease. As one of the causes of the disease is regarded the occurrence of neuronal damage in the brain resulting from ischemic condition at an attack. Accordingly, it is expected that agents having protective effects on neuronal damage in the brain after a transient ischemia, that is, neuroprotective activity, are useful for the prevention and treatment of senile dementia.

3-Sulfamoylmethyl-1,2-benzisoxazole and its alkali metal salts are known to be useful as an anticonvulsant agent [Arzneim.-Forsch./Drug Res., 30 (I), 477-483 (1980) and U.S. Pat. No. 4,172,896]. On the other hand, it is reported that phenytoin and carbamazepine, typical anticonvulsants, are effective against cerebral hypoxia [Arch. int. Pharmacodyn., 286, 282-298 (1987)].

At present, hypnonarcotic agents such as phenobarbital and thiobarbital are used in the treatment of ischemic brain damage. Their neuroprotective activity is attributed to a decrease of energy demand of neurons themselves, which results from the depression of the activity of central nervous system by them. In other words, hypnonarcotic agents exhibit neuroprotective activity by suppressing the function of neurons below physiological levels. Accordingly, for attaining the desired effect, it is necessary to administer a hypnonarcotic agent at a dose sufficient to exhibit depressant effects on the whole central nervous system. As a result, the brain stem system regulating respiration or blood pressure is depressed so that an adverse effect on respiratory or circulatory organ accompanies the protective effect of hypnonarcotic agents as a side effect.

The present inventors have found that 3-sulfamoylmethyl-1,2-benzisoxazole and its alkali metal salts have potent protective effects on cerebral hypoxia without being accompanied by such side effects as hypnonarcotic agents, and that they have an extremely potent protective effect on neuronal damage in the hippocampus which is an important region in terms of controlling emotion, memory, and the like, in contrast to the relatively weak effect of phenytoin and carbamazepine.

DISCLOSURE OF INVENTION

The present invention relates to an agent for treating ischemic brain damage containing 3-sulfamoylmethyl-1,2-benzisoxazole or an alkali metal salt thereof as an active ingredient.

From another point of view, the invention relates to a method for the prevention and/or treatment of cerebral ischemia-induced intracranial diseases or symptoms associated therewith in mammals which comprises administering to said mammals in need of such prevention and/or treatment an effective amount of 3-sulfamoylmethyl-1,2-benzisoxazole or an alkali metal salt thereof.

From a further different point of view, the invention relates to use of 3-sulfamoylmethyl-1,2-benzisoxazole or an alkali metal salt thereof for the manufacture of an agent for treating ischemic brain damage.

The alkali metal salts of 3-sulfamoylmethyl-1,2-benzisoxazole include sodium salt, potassium salt and lithium salt.

3-Sulfamoylmethyl-1,2-benzisoxazole (hereinafter occasionally referred to as the "active compound of the invention") and its alkali metal salts are known compounds as mentioned above; they can be prepared, for example, by the methods disclosed in U.S. Pat. No. 4,172,896. The active compound of the invention is represented by the following chemical structural formula:

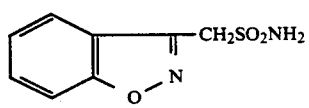

As is clear from the results of the following pharmacological tests, the active compound of the invention and its alkali metal salts show excellent pharmacological activities supporting usefulness as an agent for treating ischemic brain damage, that is to say, they show a strong protective effect on cerebral hypoxia in a very low dose. Further, they also show a very strong protective effect on neuronal damage in the hippocampus which is the important region of the brain in terms of responsibility for emotion, memory, and the like. Moreover, unlike the mode of action of hypnonarcotic agents which have so far been used in the treatment of brain ischemic damage, the protective effect of the active compound and its salts of the invention on the function of neurons is not based on the depression of the activity of cerebral nervous system; so side effects such as respiratory depression and circulatory insufficiency due to the depression of the whole central nervous system are not seen. In addition, while hypnonarcotic agents are administered only for an acute phase following cerebral ischemia, the active compound of the invention and its alkali metal salts can be administered not only for an acute phase, but also for a chronic phase after occurrence of the ischemia and for the prevention of recurrence of cerebral ischemia because of lack of hypnonarcotic activity. The active compound of the invention and its alkali metal salts have low toxicity and, consequently, high safety.

TEST 1

Protective effect on cerebral hypoxia (1) Prolonging effect on the persistent time of gasping movements in complete ischemia This test was carried out according to the method described in Arch. int. Pharmacodyn., 233, 136-144 (1978).

Male mice of STD-ddY strain weighing 22-26 g were used in groups of 5 animals. A prescribed amount of test compounds, suspended in a 0.5% aqueous tragacanth solution, was orally administered to mice at a volume of 0.1 ml per 10 g of body weight. Two hours or one hour (for carbamazepine) after the administration of test compounds, the necks of the animals were cut with scissors for decapitation. The persistent time of gasping movements in the isolated heads was measured. To control group was orally administered only the same volume of a 0.5% aqueous tragacanth solution. The $PD_{15}$ was calculated from the dose-activity relationship. The $PD_{15}$ means the dose of a test compound which prolonged the persistent time of gasping movements by 15% in comparison with that of control group. The results are shown in Table 1.

(2) Prolonging effect on survival time of mice in normobaric hypoxia

This test was carried out according to the method described in Naunyn-Schmiedeberg's Arch. Pharmacol., 334, 282-289 (1986).

Male mice of STD-ddY strain weighing 22-2.5 g were used in groups of 5 animals. A prescribed amount of test compounds, suspended in a 0.5% aqueous tragacanth solution, was orally administered to mice at a volume of 0.1 ml per 10 g of body weight. Two hours or one hour (for carbamazepine) after the administration of test compounds, each animal was taken in a 2.5-liter plastic chamber, and a mixed gas of 4% oxygen and 96% nitrogen was passed through the chamber at a rate of 4 liters/minute. There was measured the time to the death (respiratory cessation) of the animal. To control group was orally administered only the same volume of a 0.5% aqueous tragacanth solution. The $PD_{30}$ was calculated from the dose-activity relationship. The $PD_{30}$ means the dose of a test compound which prolonged the survival time by 30% in comparison with that of control group. The results are shown in Table 1.

TABLE 1

| | Protective effect on cerebral hypoxia (mice, p.o.) | |
|---|---|---|
| Test compound | Complete ischemia $PD_{15}$ | Normobaric hypoxia $PD_{30}$ |
| The active compound of the invention | 6.0 mg/kg | 29.4 mg/kg |
| Phenobarbital | 15.0 | 26.8 |
| Phenytoin | 5.5 | 22.7 |
| Carbamazepine | 5.5 | 19.6 |

As is clear from Table 1, the active compound of the invention showed protective effects on cerebral hypoxia comparable to those of phenobarbital, phenytoin and carbamazepine.

TEST 2

Protective effect on delayed neuronal death in the gerbil hippocampus following a transient ischemia This test was carried out according to the method described in Brain Res., 239, 57-69 (1982).

Male Mongolian gerbils weighing 65-85 g were used in groups of 5 or 6 animals. A prescribed amount of test compounds, suspended in a 0.5% aqueous tragacanth solution, was orally administered to animals at a volume of 0.2 ml per 100 g of body weight. To control group was orally administered only the same volume of 0.5% aqueous tragacanth solution. One hour after the administration of test compounds, the necks of the gerbils were opened by a mid line incision under ether anesthesia, and then the bilateral common carotid arteries were exposed and occluded with Zen clips to block the blood flow. After 5 minutes, the clips were released and the blood flow was restored. Animals for the sham-operated group were operated in the same manner as above except that the occlusion of the carotid arteries. After 4 days, the animals were anesthetized with pentobarbital and fixed by transcardiac perfusion with a fixative solution containing 2.5% glutaraldehyde and 2% formaldehyde in 0.1M phosphate buffer (pH 7.4) at a pressure of 120 cm $H_2O$, and then the brains were removed. After the isolated brains were kept in the same fixative solution as above overnight, they were cut into coronal sections which contained the hippocampal area 0.5-1.0 mm posterior to the most rostral tip of the hippocampus or 1.4-1.9 mm posterior to bregma. Dissected brains were dehydrated and then embedded in paraffin. From the paraffin block, 4 μm-thin sections were prepared and subjected to hematoxylin-eosin staining.

The number of morphologically intact neurons remaining in the hippocampal CA1 subfield of the above tissue specimen was measured using a computer-image digitizer (Image Research Inc., Canada, MCID model) at a magnification of 200×, and neuronal density per $mm^2$ area of the right and left hippocampus, namely, the CA1 neuronal density, was calculated.

The results are shown in Table 2. The value of the CA1 neuronal density in the table was calculated based on the average of the numbers of the remaining neurons in the right and left hippocampus of each animal. Student's t-test was used for the statistical analysis.

TABLE 2

Protective effect on delayed neuronal death in the gerbil hippocampal CA1 subfield

| Test compound | Dose (mg/kg, p.o.) | Number of animals | CA1 neuronal density (number of cells/mm$^2$ ± S.E.) |
|---|---|---|---|
| Sham operation | — | 6 | 3549 ± 281** |
| Vehicle control | — | 5 | 250 ± 64 |
| The active compound of the invention | 10 | 5 | 519 ± 28 |
|  | 30 | 5 | 2713 ± 228** |
|  | 100 | 5 | 3326 ± 49** |
| Phenytoin | 30 | 5 | 228 ± 87 |
|  | 100 | 5 | 1464 ± 503 |
| Carbamazepine | 10 | 5 | 482 ± 272 |
|  | 30 | 6 | 932 ± 353 |
|  | 100 | 5 | 1235 ± 330* |

*Significantly different from the value of vehicle control ($p < 0.05$).
**Significantly different from the value of vehicle control ($p < 0.01$).

As shown in Table 2, the active compound of the invention at a dose of 30 mg/kg exhibited extremely strong protective effect on delayed neuronal death in the gerbil hippocampal CA1 subfield and at a dose of 100 mg/kg almost completely prevented the delayed neuronal death. On the other hand, phenytoin and carbamazepine only showed relatively weak protective effect even at a dose of 100 mg/kg.

TEST 3

Hypnonarcotic activity

This test was carried out according to the method described in Japan. J. Pharmacol., 13, 259-273 (1963).

Male mice of STD-ddY strain weighing 22-26 g were used in groups of 5-10 animals. A prescribed amount of test compounds, suspended in a 0.5% aqueous tragacanth solution, was orally administered to mice at a volume of 0.1 ml per 10 g of body weight. After the administration of test compounds, the animals were observed for the presence of the righting reflex at hourly intervals. When the righting reflex was lost for 60 minutes or more, it was judged that a test compound showed hypnonarcotic effect at a given dose. The HD$_{50}$ was calculated by Probit method. The HD$_{50}$ means the dose of a test compound which produced hypnonarcotic effect in 50% of animals. The results are shown in Table 3.

TEST 4

Acute toxicituy

Male mice of STD-ddY strain weighing 22-26 g were used in groups of 5-10 animals. A prescribed amount of test compounds, suspended in a 0.5% aqueous tragacanth solution, was orally administered to mice at a volume of 0.2 ml per 10 g of body weight. The mortality was observed for 7 days. The LD$_{50}$, namely, the dose of a test compound which caused death in 50% of animals, was calculated by Probit method. The results are shown in Table 3.

TABLE 3

Hypnonarcotic activity and acute toxicity (mice, p.o.)

| Test compound | Hypnonarcotic activity HD$_{50}$ | Acute toxicity LD$_{50}$ |
|---|---|---|
| The active compound of the invention | 934 mg/kg | 1892 mg/kg |
| Phenobarbital | 97 | 201 |
| Phenytoin | >200* | 363 |
| Carbamazepine | 345 | 1700 |

*The HD$_{50}$ could not be determined due to appearance of clonic convulsion in all mice and of death in some mice at a dose of 200 mg/kg or more.

As is clear from Table 3, the hypnonarcotic activity of the active compound of the invention was about one-tenth of that of phenobarbital, and further the toxicity of the compound was weak.

The active compound of the invention and its alkali metal salts have extremely strong neuroprotective activity, as well as potent anticerebral hypoxic activity which are separated well from hypnonarcotic activity and toxicity. Therefore, they can be used for the prevention and treatment of cerebral ischemia-induced intracranial diseases or various symptoms associated therewith in mammals including human beings. Examples of the intracranial diseases include cerebral infarction caused by cerebral thrombosis or cerebral embolism, intracerebral hemorrhage, subarachnoid hemorrhage, head injury, brain tumor, cerebral meningitis, and cerebral edema, and examples of the symptoms associated therewith include disturbance of consciousness, neuropathy, dementia, subjective symptom such as dizziness, headache, migraine, nausea, or vomiting, and enhancement of intracranial pressure during or after a surgical operation on the brain. The active compound of the invention and its alkali metal salts can be administered through any of oral, parenteral and intrarectal routes. The dosage of them may vary depending on the administration route, the kinds of diseases, the severity of symptoms, the age of patients, and the like, but is usually in the range of 1 to 50 mg/kg/day, which may be administered at a time or in several times.

The active compound of the invention and its alkali metal salts may be used as an agent for treating ischemic brain damage as such or in the form of a pharmaceutical composition in admixture with a pharmaceutical carrier. The pharmaceutical compositions may be in the dosage forms such as tablets, capsules, granules, fine granules, powders, syrups, injections, suppositories, and the like. They can be prepared by conventional methods.

The pharmaceutical carrier includes substances which are commonly used in the pharmaceutical field and do not react with the active compound of the invention or its alkali metal salts. Examples of the pharmaceutical carrier for the preparation of tablets, capsules, granules, fine granules and powders include diluents such as lactose, corn starch, sucrose, mannitol, calcium sulfate, and microcrystalline cellulose; disintegrators such as sodium carboxymethylcellulose, modified starch, and calcium carboxymethylcellulose; binders such as methylcellulose, gelatin, acacia, ethylcellulose, hydroxypropylcellulose, and polyvinylpyrrolidone; lubricants such as light anhydrous silicic acid, magnesium stearate, talc, and hydrogenated oil; or the iike. In the preparation of tablets, they may be coated in a conventional manner by using conventional coating agents such as carnauba wax, hydroxypropyl methylcellulose, macrogol, hydroxypropyl methylphthalate, cellulose acetate phthalate, sucrose, titanium dioxide, sorbitan fatty acid ester, calcium phosphate, and the like.

Examples of the carriers for the preparation of syrups include sweetening agents such as sucrose, glucose, fructose, and sorbitol; suspending agents such as acacia, tragacanth, sodium carboxymethylcellulose, methylcellulose, sodium alginate, microcrystalline cellulose, and veegum; dispersing agents such as sorbitan fatty acid ester, sodium lauryl sulfate and polysorbate 80; or the like. In the preparation of syrups, conventional flavoring agents, aromatic substances, preservatives, or the like may optionally be added. The syrups may be in the form of a dry syrup which is dissolved or suspended before use.

Examples of the bases for the preparation of suppositories include cacao butter, glycerin saturated fatty acid ester, glycerogelatin, macrogol, or the like. In the preparation of suppositories, conventional surface active agents, preservatives, or the like may optionally be added.

Injections are generally prepared by dissolving an alkali metal salt of the active compound of the invention in distilled water for injection, and thereto may optionally be added conventional solubilizers, buffering or pH adjusting agents, isotonic agents, pain-reducing agents, preservatives, or the like. The injections may be in the form of a suspension of the active compound of the invention in distilled water for injection or vegetable oil, and thereto may optionally be added conventional bases, suspending agents, or the like. They may be also in the form of powders or lyophilized products to be dissolved in a suitable vehicle before use, and thereto may optionally be added conventional diluents, or the like.

These pharmaceutical compositions usually contain the active compound of the invention or its alkali metal salt as an active ingredient in an amount of 0.5% by weight or more, preferably 10 to 70% by weight, based on the total weight of a composition. These compositions may optionally contain other therapeutically active compounds as mentioned below.

The agent for treating ischemic brain damage according to the present invention can be administered together with other drugs: agents for reducing intracranial pressure, such as glyceol (trademark; a combined agent of glycerin and fructose) and mannitol; antioxidant agents such as vitamin E, vitamin C and vitamin K; non-steroidal antiinflammatory agents such as indomethacin, ibuprofen, sulindac and tolmetin; calcium antagonists such as nicardipine, nimodipine and flunarizine; thromboxane antagonists; 5-lipoxygenase inhibitors; prostaglandin derivatives as disclosed in U.S. Pat. No. 4,499,085; and the like.

BEST MODE FOR CARRYING OUT THE INVENTION

The present invention is illustrated by the following Examples, but should not be construed to be limited thereto.

EXAMPLE 1

| Tablets | |
|---|---|
| 3-Sulfamoylmethyl-1,2-benzisoxazole | 100 g |
| Lactose | 35 g |
| Corn starch | 17 g |
| Microcrystalline cellulose | 40 g |
| Hydroxypropylcellulose | 6 g |
| Light anhydrous silicic acid | 1 g |

| -continued | |
|---|---|
| Tablets | |
| Magnesium stearate | 1 g |

The first four components are blended, kneaded after the addition of an aqueous solution of the hydroxypropylcellulose, dried and granulated. To these granules are added the magnesium stearate and light anhydrous silicic acid, and the resulting mixture is compressed into 1,000 tablet cores each weighing 200 mg. These are coated to form film-coated tablets by a conventional method, employing hydroxypropyl methylcellulose, macrogol, titanium dioxide, talc and light anhydrous silicic acid.

EXAMPLE 2

| 20% Powders | |
|---|---|
| 3-Sulfamoylmethyl-1,2-benzisoxazole | 200 g |
| Lactose | 719 g |
| Hydroxypropylcellulose | 20 g |
| Light anhydrous silicic acid | 1 g |

Using a high speed mixer, the above all components are blended, sprayed with an ethanolic solution (200 g) containing ethylcellulose (40 g) and hydroxypropylcellulose (20 g), and made into granules. These are dried and regulated in size to give 20% powders.

EXAMPLE 3

| Injections | |
|---|---|
| Sodium salt of 3-sulfamoylmethyl-1,2-benzisoxazole | 276 g |
| Glycine | 10 g |
| 1N Sodium hydroxide | a sufficient quantity |
| Distilled water for injection | a sufficient quantity |
| | To make 5 liters |

The first two components are dissolved with stirring in a part of the distilled water for injection and adjusted to pH 11.5 by slowly adding the 1N sodium hydroxide and thereto is added the remaining distilled water for injection. The resulting solution is filtered through a Membrane filter (0.22 μm). The filtrate is filled into ampules so that each contains 5 ml. After replacement of the air by nitrogen, the ampules are sealed and subjected to steam sterilization under pressure at 121° C. for 20 minutes to give 1,000 injections.

EXAMPLE 4

| Injections | |
|---|---|
| 3-Sulfamoylmethyl-1,2-benzisoxazole | 500 g |
| Sodium carbonate | 20 g |
| 1N Sodium hydroxide | a sufficient quantity |
| Propylene glycol | 4 liters |
| Ethanol | 1 liter |
| Distilled water for injection | a sufficient quantity |
| | To make 10 liters |

The four components, namely, the 3-sulfamoyl-methyl-1,2-benzisoxazole, sodium carbonate, propylene glycol and ethanol, are suspended in a part of the distilled water for injection and made a clear solution of pH 11.0 by slowly adding the 1N sodium hydroxide with stirring, and thereto is added the remaining distilled water for injection. The resulting solution is filtered through a Membrane filter (0.22 μm). The filtrate is filled into ampules so that each contains 10 ml. After replacement of the air by nitrogen, the ampules are sealed and subjected to steam sterilization under pressure at 121° C. for 20 minutes to give 1,000 injections.

INDUSTRIAL APPLICABILITY

As mentioned above, 3-sulfamoylmethyl-1,2-benzisoxazole and its alkali metal salts are useful as an agent for treating ischemic brain damage for the prevention and treatment of cerebral ischemia-induced intracranial diseases or various symptoms associated therewith in mammals including human beings.

We claim:

1. A method for the treatment of cerebral ischemia-induced intracranial diseases or symptoms associated therewith in mammals which comprises administering to said mammals in need of such treatment an effective amount of 3-sulfamoylmethyl-1,2-benzisoxazole or an alkali metal salt thereof.

2. A method according to claim 1, in which the daily dosage of 3-sulfamoylmethyl-1,2-benzisoxazole or an alkali metal salt thereof is in the range of 1 to 50 mg per kg of body weight of a mammal.

3. A method according to claim 1, in which the cerebral ischemia-induced intracranial diseases or symptoms associated therewith is cerebral infarction caused by cerebral thrombosis or cerebral embolism, intracerebral hemmorrage, subarachnoid hemorrhage, head injury, brain tumor, cerebral meningitis, cerebral edema, disturbance of consciousness, neuropathy, dementia, dizziness, headache, migraine, nausea, vomiting, or enhancement of intracranial pressure during or after a surgical operation on the brain.

4. A method according to claim 2, in which the cerebral ischemia-induced intracranial diseases or symptoms associated therewith is cerebral infarction caused by cerebral thrombosis or cerebral embolism, intracerebral hemorrhage, subarachnoid hemorrhage, head injury, brain tumor, cerebral meningitis, cerebral edema, disturbance of consciousness, neuropathy, dementia, dizziness, headache, migraine, nausea, vomiting, or enhancement of intracranial pressure during or after a surgical operation on the brain.

* * * * *